US00PP29587P2

(12) United States Plant Patent
Dozier, Jr. et al.

(10) Patent No.: US PP29,587 P2
(45) Date of Patent: Aug. 14, 2018

(54) KIWI PLANT NAMED 'AU GULF COAST GOLD'

(50) Latin Name: ***Actinidia chinensis* Planch**
Varietal Denomination: AU Gulf Coast Gold

(71) Applicant: Auburn University, Auburn, AL (US)

(72) Inventors: W. Alfred Dozier, Jr., Opelika, AL (US); James A. Pitts, Clanton, AL (US); James D. Spiers, Auburn, AL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 15/330,677

(22) Filed: Oct. 26, 2016

(51) Int. Cl.
*A01H 5/08* (2018.01)

(52) U.S. Cl.
USPC ..... Plt./156
CPC ..... *A01H 5/08* (2013.01)

(58) Field of Classification Search
USPC ..... Plt./156
CPC ..... A01H 5/08; A01H 5/00; A01H 5/0806
See application file for complete search history.

(56) References Cited

U.S. PATENT DOCUMENTS

| | | | |
|---|---|---|---|
| PP11,066 | P | 9/1999 | Lowe et al. |
| PP20,994 | P2 | 5/2010 | Dozier, Jr. et al. |
| PP21,005 | P2 | 5/2010 | Dozier, Jr. et al. |
| PP22,140 | P2 | 9/2011 | Dozier, Jr. et al. |
| PP22,159 | P3 | 9/2011 | Dozier, Jr. et al. |
| PP22,191 | P2 | 10/2011 | Dozier, Jr. et al. |

OTHER PUBLICATIONS

Huang, H., S. Wang, Z. Zhang, and J. Gong. 2003. Exploration of Actinidia genetic resources and development of ciwifruit industry in China. Acta Hort 610:29-43.

Jaeger, S.R., R. Harker, C.M. Triggs, A. Gunson, R.L. Campbell, R. Jackman and C. Requejo-Jackman. 2011. Determining consumer purchase intentions: The importance of dry matter, size and price of kiwifruit. J. Food Sci. 76 (3):177-184.

Jiang, Z, S. Wang, R. Huang, Z. Zhang, and H. Huang. 2005. 'Wuzhi No3' kiwifruit. HortScience 40(6):1923-1924.

Patterson, K., J. Burdon and N. Lallu. 2003 'Hort 16A' kiwifruit: Progress and issues with commercialization. Acta Hort. 610:267-273.

Wall et al., "Determining a Maturity Index and the Effect of Chilling Requirements, and Cytokinin Applications on Three few Kiwi Cultivars," Thesis—Degree of Master of Science, Auburn University, Aug. 2006, 87 pages.

Wall et al., "Vegetative and Floral Chilling Requirement of Four New Kiwi Cultivars of Actinidia chinensis and A. deliciosa," (Hort Science 43(3):644-647, Jun. 2008.

Wang, M.Y., E. MacRae, M. Wohlers and K. Marsh. 2011. Changes in volatile production and sensory quality of kiwifruit during fruit maturation in Actinidia deliciosa 'Hayward' and A. chinensis 'Hort 16A'. Postharvest Biol. and Technol. 59:16-24.

*Primary Examiner* — June Hwu
(74) *Attorney, Agent, or Firm* — Andrus Intellectual Property Law, LLP

(57) ABSTRACT

'AU Gulf Coast Gold' is a new golden-fleshed cultivar of *Actinidia chinensis* Planch with a low chilling requirement. 'AU Gulf Coast Gold' fruit is large, cylindrical and uniform in shape with yellow flesh that has a thick sweet flavor and delicious taste. 'AU Gulf Coast Gold' fruit has a high percent soluble solids and dry matter content. Vegetative bud burst begins in late March to early April and flowering begins on average April 18-20 in central Alabama. Fruit typically reaches maturity September 21-25 in central Alabama with an internal color hue of less than 103°.

8 Drawing Sheets

Latin name of the genus and species of the plant claimed: *Actinidia chinensis* Planch.

Variety denomination: 'AU GULF COAST GOLD'.

BACKGROUND OF THE INVENTION

The genus *Actinidia* is native to China and is comprised of more than 50 species. *Actinidia chinensis* Planch and *Actinidia deliciosa* (A. Chev). C.F. Liang and A.R. Ferguson are the two most important commercial *Actinidia* species. *Actinidia chinensis* is more precocious and productive and the fruit are more attractive in appearance with less pubescence on the fruit skin than *A. deliciosa.*

Kiwifruit plants are dioecious and have vegetative and compound buds with flower clusters produced in the leaf axils of the first four to six nodes of shoots arising from buds on one year old shoots. Male and female flowers are perfect morphologically. The female flower contains some anthers, but only the stigma is functional, whereas the flower on a male vine typically produces 125-185 large anthers that surround a small vestigial stigma. For pollination and fruit set to occur, the female plant must be in close proximity of a male plant whose bloom period occurs at the same time as the female plant's bloom period.

'AU Gulf Coast Gold' is a new golden-fleshed cultivar of *Actinidia chinensis* Planch. It is a bud mutation that occurred on a 'AU Golden Sunshine' (U.S. Plant Pat. No. 22,159) plant in a cultivated and maintained orchard to evaluate kiwifruit cultivar performance at Fairhope, Baldwin County, Ala. Based on the genetic marker comparison of 'AU Golden Sunshine' (patented) and 'AU Gulf Coast Gold', the genetic distinction between these two cultivars is strong (Table 1). Wood from this plant was grafted onto *Actinidia deliciosa* kiwifruit plants at Clanton, Chilton County, Ala., where it has been grown and evaluated since 1999. 'AU Gulf Coast Gold' has been asexually reproduced at Auburn, Clanton and Reeltown, Ala. and Marysville and Reedly, Calif., USA by rooting softwood and hardwood cuttings, by whip and cleft grafting and tissue culture. Genetics have been stable through succeeding asexual propagation.

'AU Gulf Coast Gold' fruit is large, cylindrical and uniform in shape with golden flesh that has a thick sweet flavor and delicious taste. 'AU Gulf Coast Gold' fruit has high percent soluble solids and dry matter typically higher than 'AU Golden Sunshine' (patented) and comparable to slightly lower than 'Hort 16A' *A. chinensis* (U.S. Plant Pat. No. 11,066) (Table 2). Dry matter content, a positively correlated indicator of soluble solids content of kiwifruit when allowed to ripen, appears to be closely related to fruit development period, and 'AU Gulf Coast Gold' has a longer fruit development period compared to 'AU Golden Sunshine' (patented) and a shorter fruit development period compared to 'Hort 16A' (patented). Increasing dry matter content has been shown to increase purchase likelihood for kiwifruit (Jaeger et al., 2011). 'AU Gulf Coast Gold' bloom period begins 1-2 days before 'AU Golden Sunshine' (patented), and is completed 2 days before 'AU Golden Sunshine' (patented) bloom period (Table 3).

SUMMARY OF THE INVENTION

The present invention relates to a new and distinct early to mid season ripening yellow fleshed kiwifruit cultivar that produces cylindrical, uniformly shaped fruit with the stylar end rounded to somewhat pointed, and the shape on the stalk end rounded and narrow. Fruit skin color is grey brown (N199B) color with medium density of uniform short lanulose hairs on fruit skin surface (Table 4). At maturity, the fruit surface appears brown due to the lanulose hairs.

The new cultivar is able to be asexually reproduced by softwood and hardwood cuttings or by grafting onto a rootstock. The unique characteristics come true to form and are established and transmitted through succeeding asexual propagations. 'AU Gulf Coast Gold' has been asexually propagated by rooting softwood and hardwood cuttings, and by whip and cleft grafting in Alabama and California, USA.

Kiwifruit plants are dioecious and have vegetative and compound buds with flower clusters produced in the leaf axils of the first four to six nodes. Male and female flowers are perfect morphologically. The female flower contains some anthers but only the stigma is functional whereas the flower on a male vine typically produces 125 to 185 large anthers that surround a small, vestigial stigma. In Alabama, 'AU Golden Tiger' (U.S. Plant Pat. No. 22,140) and 'Chieftain' (unpatented) are the male cultivars used as pollinizers. 'AU Golden Tiger' (patented) bloom period begins with 'AU Gulf Coast Gold', and 'Chieftain' bloom period begins during the latter part of 'AU Gulf Coast Gold' bloom period.

Kiwifruit buds enter endodormancy during winter, which requires a minimum number of chilling hours for maximum budbreak and bloom. Floral uniformity and density in spring is directly related to the amount of chilling received during winter. It is believed the more accurate measure of chilling hours is Richardson units, which are defined as the accumulated hours between 0° C. and 7° C.

For maximum bud break and flowering of 'AU Golden Sunshine' (patented) to occur it was determined that 700 hours of chilling was required and after the chilling requirements was met 15000 growing degree hours were necessary for bud break (Wall et al. 2008). 'AU Gulf Coast Gold' has similar chilling requirement as 'AU Golden Sunshine' (patented). The high growing degree hours requirement results in a late bud break and blooming period that typically occurs after the danger of a late spring frost. 'AU Gulf Coast Gold' has performed well in central Alabama where it receives an average winter chilling of 800-1200 hours.

In central Alabama, 'AU Gulf Coast Gold' flowers begin to open ~2 days before 'AU Golden Sunshine' (patented) and its fruit ripens several weeks after 'AU Golden Sunshine' in the fall. 'AU Gulf Coast Gold' reaches harvest maturity 21-30 days after 'AU Golden Sunshine' (patented) (Table 2). 'AU Gulf Coast Gold' has a cylindrical fruit shape, as does 'AU Golden Sunshine' (patented). However, the stylar end is rounded to somewhat pointed in comparison to the rounded stylar end of 'AU Golden Sunshine' (patented). The shape of the shoulder on the stalk end of 'AU Gulf Coast Gold' is rounded and narrow in comparison to the rounded to flat shoulder on the stalk end of 'AU Golden Sunshine' (patented).

DETAILED BOTANICAL DESCRIPTION

Figure 1:
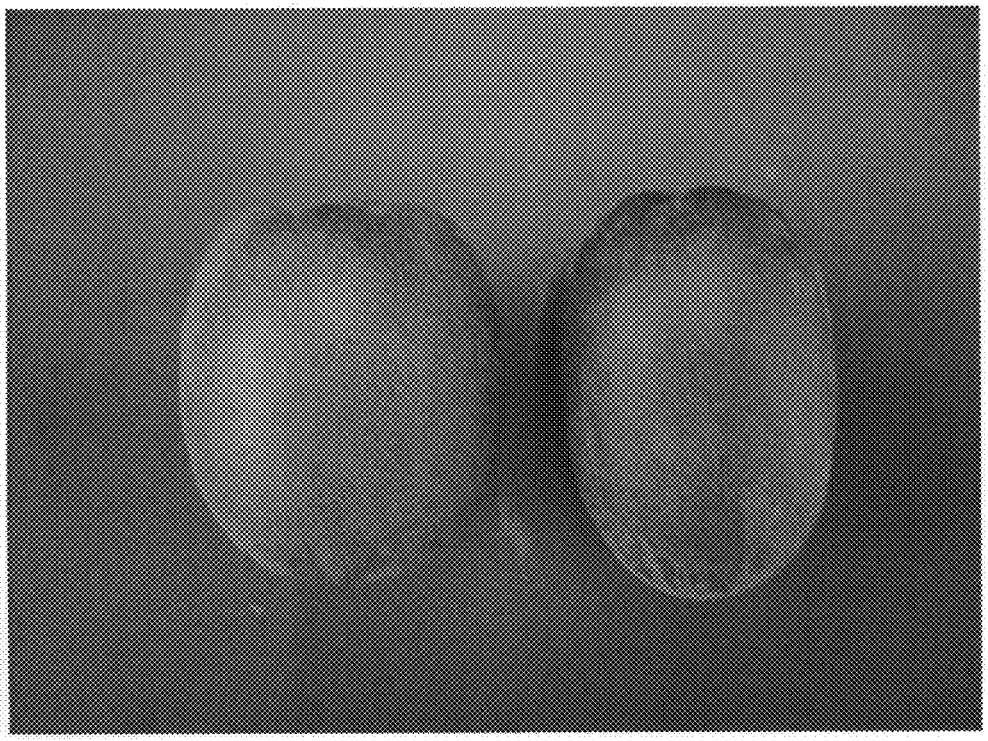
FIG. 1 is a photograph of 'AU Golden Sunshine' (patented) fruit (on left) and 'AU Gulf Coast Gold' fruit (on right).
Figure 2:
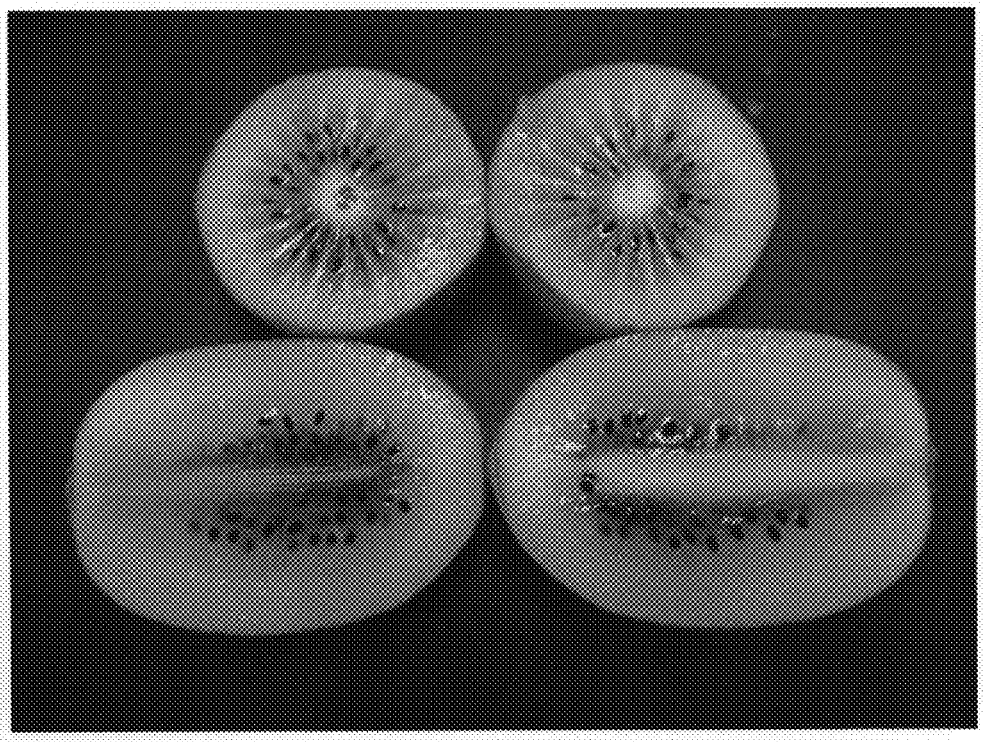
FIG. 2 is a photograph of 'AU Gulf Coast Gold' fruit cut in half lengthwise and widthwise to illustrate flesh color.
Figure 3:
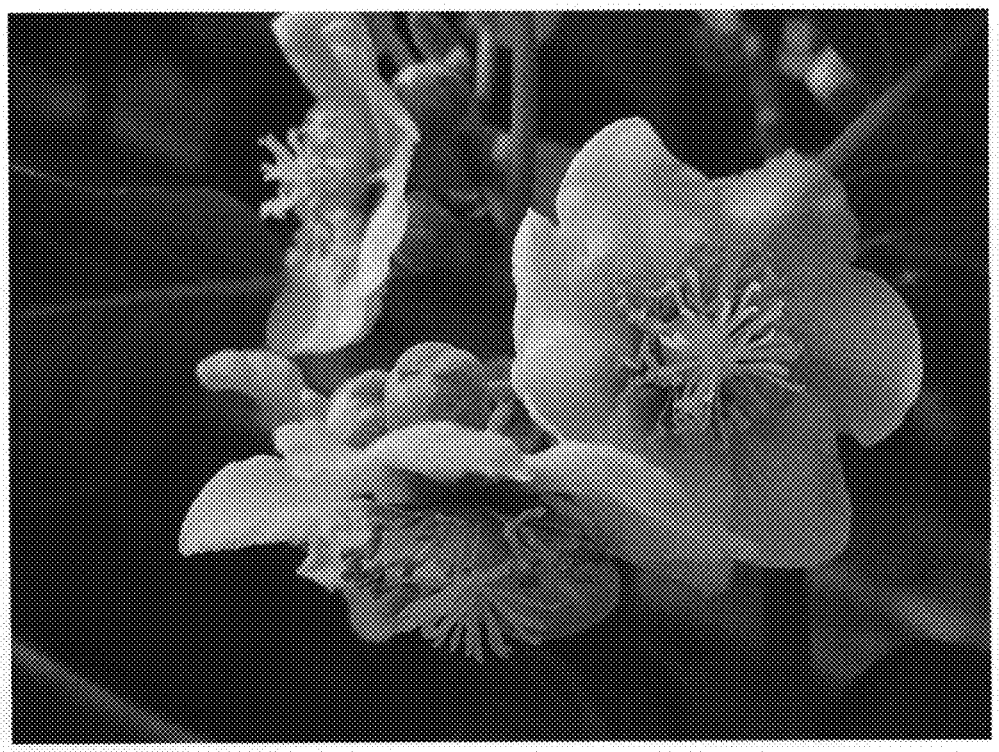
FIG. 3 is a photograph of 'AU Gulf Coast Gold' flowers and flower buds on a 16-year old grafted plant.
Figure 4:
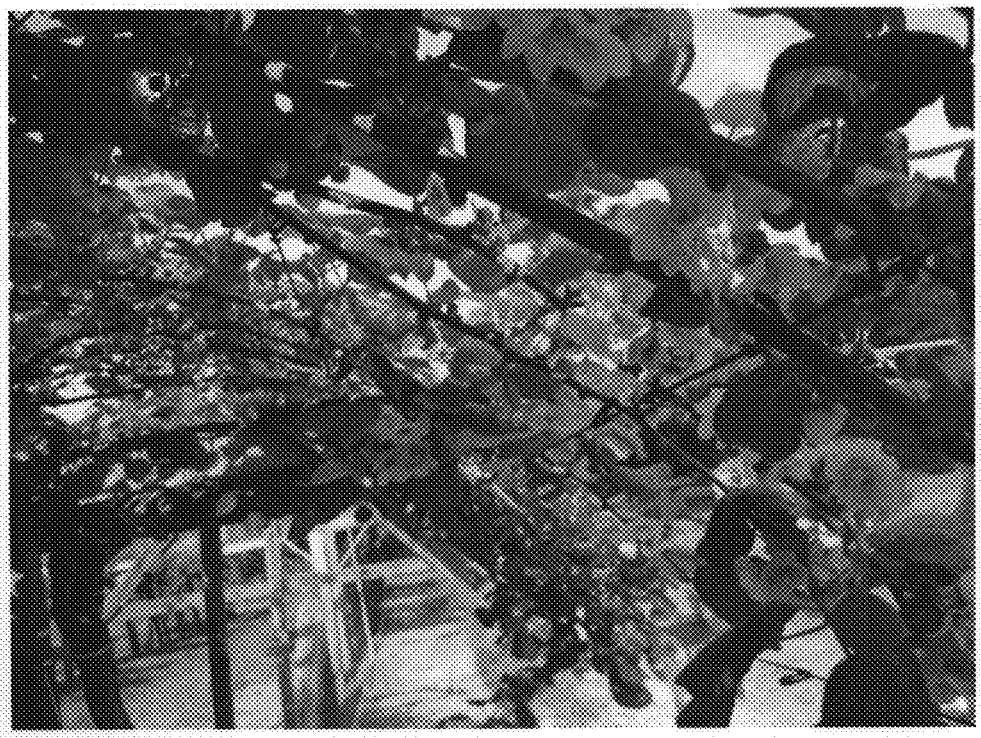
FIG. 4 is photograph of 'AU Gulf Coast Gold' flower bud density on 16-year old grafted plant.
Figure 5:
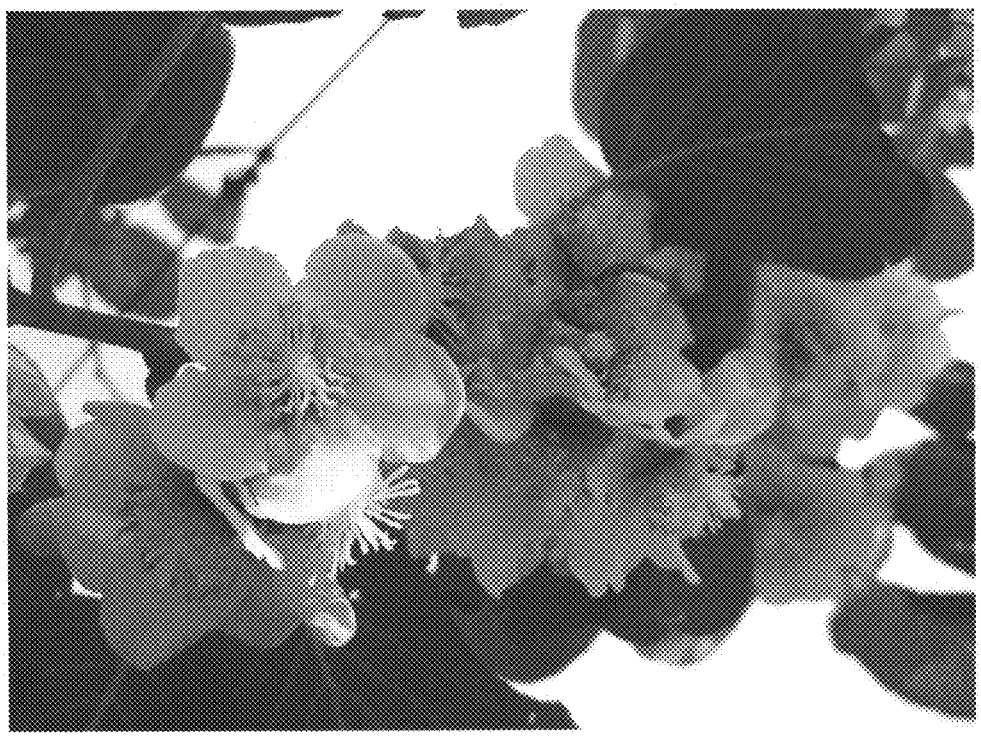
FIG. 5 is a photograph of 'AU Gulf Coast Gold' flowers at different stages of development to illustrate flower bud density on a 16-year old grafted plant.
Figure 6:
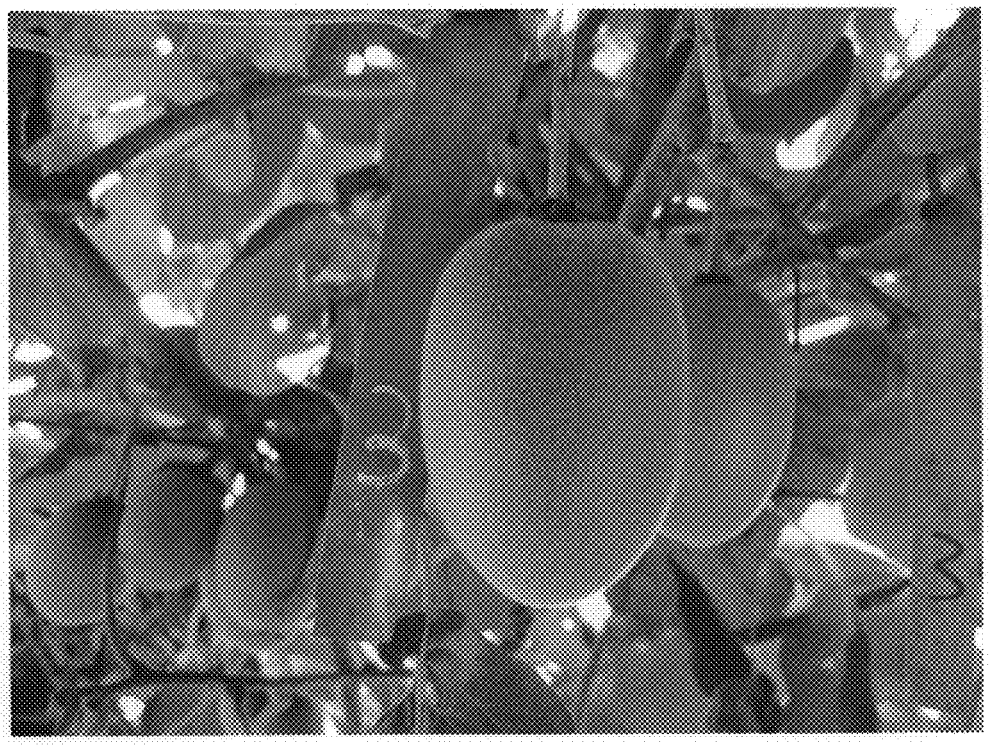
FIG. 6 is a photograph of 'AU Gulf Coast Gold' fruit on 16-year old grafted plant.
Figure 7:
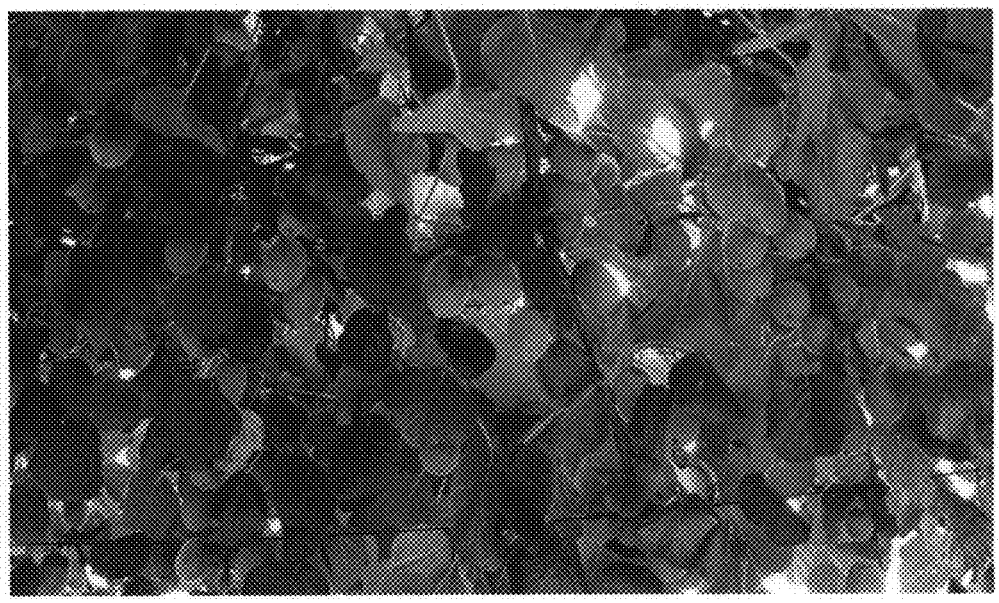
FIG. 7 is a photograph of 'AU Gulf Coast Gold' fruit load on vine on a 14-year old grafted plant.
Figure 8:
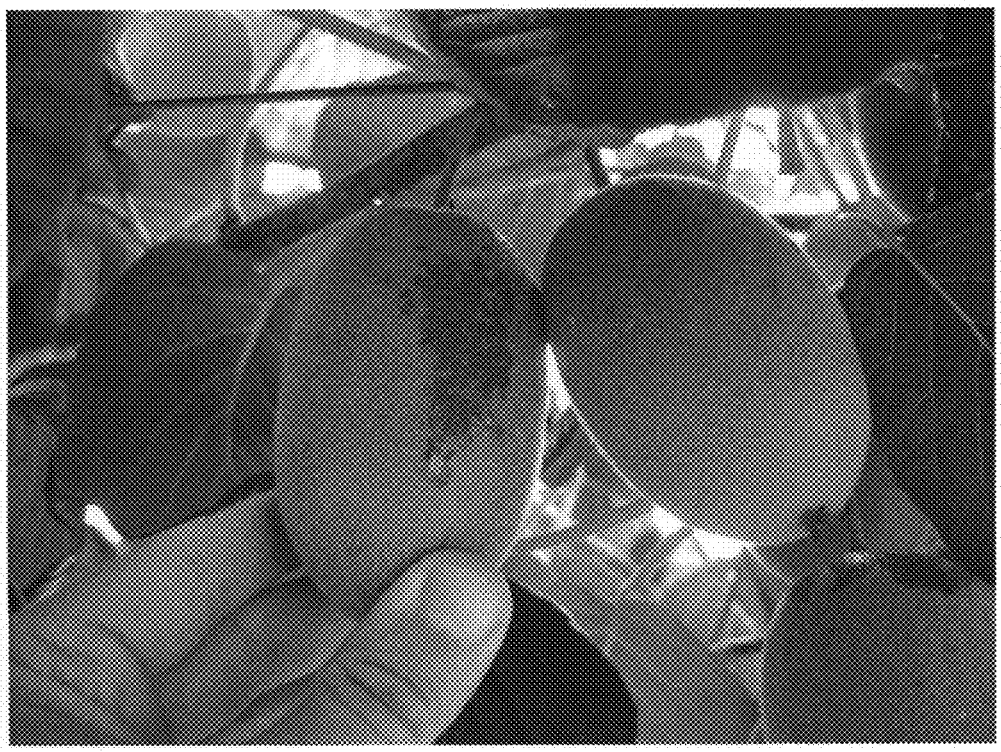
FIG. 8 is a photograph of 'AU Gulf Coast Gold' fruit on 16-year old grafted plant.

Kiwifruit plants are large deciduous shrubs that originated in China and are dioecious, can climb up to 25 feet, and have alternated, broadly rounded petiolate leaves. The cream-colored flowers that grow in axillary cymes mature into ovate to oblong fruits (berries) with brownish, hairy skins. There are over 50 species in the genus *Actinidia*. The two *Actinidia* species of the most commercial importance are *deliciosa* and *chinensis*. The kiwifruit plant is dioecious thereby requiring male pollenizers in the presence of the female plants to ensure fruit production. The male and female plants bloom period has to be at the same time for pollination to occur. The bloom period varies with each cultivar depending upon the chilling requirement and the growing degree hour requirement after the chilling requirement has been met. *Actinidia* are temperate zone plants that prefer well-drained moist and rich soil and grows well in full sun or part-shade.

The new cultivar 'AU Gulf Coast Gold' is pistillate, with imperfect flowers, e.g. the flowers produce only sterile pollen and thus require a pollenizer for fruit production. The male cultivars 'AU Tiger' (patented) and 'Chieftain' (unpatented) are pollenizers used with 'AU Gulf Coast Gold'. The bloom period of 'AU Gulf Coast Gold' starts about April 18$^{th}$ in central Alabama, typically ~2 days before the 'AU Golden Sunshine' (patented) bloom period.

The new cultivar can be asexually reproduced by softwood and hardwood cuttings or by grafting onto a seedling or cutting grown rootstock. The unique characteristics come true to form and are established and transmitted through succeeding asexual propagations.

'AU Gulf Coast Gold' is a bud mutation that occurred on a 'AU Golden Sunshine' (U.S. Plant Pat. No. 22,159) plant in a kiwifruit cultivar evaluation planting at Fairhope, Baldwin County, Ala. Based on the genetic marker comparison of 'AU Golden Sunshine' (patented) and 'AU Gulf Coast Gold', the genetic distinction between these two cultivars is strong (Table 1).

TABLE 1

Genetic marker comparison of 'AU Golden Sunshine' (patented) and 'AU Gulf Coast Gold'[z].

| Variety | 554[y] | 559[x] | 565[w] | 566[v] |
|---|---|---|---|---|
| AU Golden Sunshine | 142,**152**[u], **162, 164** | **131, 163** | **95**,107 | **84**,86,**88**,102 |
| AU Gulf Coast Gold | 150,**152, 162, 164** | **131, 163**,172 | 88,93,**95**,98 | **84,88**,92,100 |

[z]DNA was extracted from leaf tissue. PCR was performed by using 4 SSR (microsatellite) markers. Capillary electrophoresis was performed using ABI3100 Genetic Analyzer. Data was analyzed using GeneScan and Genotyper.
[y]Marker 554 - UDK96-026
[x]Marker 559 - UDK96-037
[w]Marker 565 - UDK97-406
[v]Marker 407 - UDK97407
[u]Common alleles in bold type for both varieties.

'AU Gulf Coast Gold' fruit has high percent soluble solids and dry matter typically higher than 'AU Golden Sunshine' (patented) and comparable to slightly lower than 'Hort 16A' *A. chinensis* (U.S. Plant Pat. No. 11,066) (Table 2).

TABLE 2

Harvest date[z] and fruit quality[y] attributes at harvest of three *Actinidia chinensis* Planch. var. *chinensis* cultivars grown in central Alabama.

| Cultivar | 2014 Harvest Date | 2015 Harvest Date | Firmness (kg) | Soluble Solids (%) | Dry Matter (%) | Internal Color (hue°) |
|---|---|---|---|---|---|---|
| 'AU Golden Sunshine' | Sept. 4 | Aug. 25 | 5.5 ± 1.8 | 8.2 ± 2.3 | 17.9 ± 0.012 | 103.1 ± 2.5 |
| 'AU Gulf Coast Gold' | Sept. 25 | Sept. 21 | 4.6 ± 0.9 | 8.4 ± 0.8 | 21.2 ± 0.007 | 102.9 ± 2.7 |
| 'HORT 16A' | Oct. 9 | Oct. 19 | 5.2 ± 1.0 | 12.9 ± 3.0 | 22.2 ± 0.007 | 103.6 ± 2.9 |

[z]Harvest date for each cultivar was based primarily on an internal color of <104 hue°.
[y]Means derived from 10 fruit/year at specified harvest date.

'AU Gulf Coast Gold' bloom period begins 1-2 days before 'AU Golden Sunshine' (patented), and is completed 2 days before 'AU Golden Sunshine' (patented) bloom period (Table 3).

TABLE 3

Flower development of 'AU Golden Sunshine' (patented) and 'AU Gulf Coast Gold' in 2009, 2010, and 2016.

| 2009 | | | | | | |
|---|---|---|---|---|---|---|
| Cultivar | Apr. 17 | Apr. 20 | Apr. 24 | Apr. 27 | Apr. 29 | May 1 |
| AU Golden Sunshine | Bud swell | Popcorn Stage | 10-30% Bloom | Full Bloom | 10-40% Petal Fall | Petal Fall |
| AU Gulf Coast Gold | Buds Cracking | Popcorn Stage | 20-50% Bloom | Full Bloom | 60-80% Petal Fall | Petal Fall |

TABLE 3-continued

Flower development of 'AU Golden Sunshine' (patented) and 'AU Gulf Coast Gold' in 2009, 2010, and 2016.

| 2010 | | | | | | |
|---|---|---|---|---|---|---|
| | Apr. 21 | Apr. 23 | Apr. 26 | Apr. 28 | Apr. 30 | May 3 |
| AU Golden Sunshine | Bud swell | Popcorn Stage | 80% Bloom | 90% Bloom | Full Bloom | Petal Fall |
| AU Gulf Coast Gold | Popcorn Stage | 50% Bloom | 70-100% Bloom | Full Bloom | Some Petal Fall | Petal Fall |

| 2016 | | | | |
|---|---|---|---|---|
| Apr. 17 | Apr. 21 | Apr. 25 | Apr. 27 | |
| AU Golden Sunshine | Popcorn Stage | 30-40% Bloom | 80% Bloom | Petal Fall |
| AU Gulf Coast Gold | 10-% Bloom | 40-50% Bloom | Full Bloom | Petal Fall |

The average plant height and spread for 'Au Gulf Coast Gold' was limited by pruning the plants and training them to a limited space of 8'×16' on top of trellis. The remaining botanical information is provided below in Table 4.

TABLE 4

Botanical description of 'AU Gulf Coast Gold' and comparison to 'AU Golden Sunshine'

| | 'Gulf Coast Gold' | 'Golden Sunshine' |
|---|---|---|
| PLANT | | |
| Plant hardiness | Has performed well in zones 8A & 8B | |
| Plant: sex expression | female (flower imperfect) | |
| Plant: ploidy | diploid | (2n = 2x = 58) |
| Plant: vigor | strong | |
| Young shoot: hairs | present | |
| Young shoot: density of hairs | medium | |
| Young shoot: type of hairs | short | |
| Young shoot: anthocyanin coloration of growing tip | absent (stem color - 152B) | |
| Young shoot: anthocyanin coloration of leaf axil | absent (stem color - 152B) | |
| Insect pest susceptibility | White peach scale (*Pseudaulacas pispentagona Targioni*) leaffooted bug (*Leptoglossus phyllopus Linnaeus*) | |
| Diseases | None observed | |
| STEM | | |
| Stem: coloration of leaf axil | Grey-brown, N199A | |
| Stem: diameter | medium | |
| Stem base diamenter | mean 12.9 mm (range 9.5-18.3 mm) [20] | |
| Stem mid section diameter | mean 9.9 mm (range 7.3-12.7) [20] | (range 7.4-12.5 mm) |
| Stem: dormant bud diameter | 4.3 mm (2.4-6.0) [20] | 4.2 mm (2.5-6.1) |

TABLE 4-continued

Botanical description of 'AU Gulf Coast Gold' and comparison to 'AU Golden Sunshine'

| | 'Gulf Coast Gold' | 'Golden Sunshine' |
|---|---|---|
| Stem: color on upper side of shoot | Grey-brown (N199B) | grey-brown (N199A) |
| Stem: character of bark | smooth | |
| Stem: hairs | few | |
| Stem: conspicuousness of lenticels | weak | |
| Stem: number of lenticels | few | |
| Stem: color of lenticels | greyed-orange (N-167A) | brownish-white |
| Stem: size of bud support | large | |
| Stem: visibility of bud (dormant canes) | visible | |
| Stern: number of hairs visible on bud (dormant canes) | high | |
| Stem: leaf scar | mean length 6.1 mm (5.8-7.2 mm) mean width 5.6 mm (5-6.5 mm) | mean length 5.5 mm (4.7-5.9 mm) mean width 5.7 mm (5-6.3 mm) |
| LEAF (Mature) | | |
| Leaf shape: | orbicular to broadly ovate: as broad as long, occasionally broader than long | broadly cordate to orbicular |
| Leaf base shape: | round to cordate, with lobes touching to occasionally overlapping; rarely broadly | rounded to cordate; lobes not overlapping |
| Leaf tip shape: | rounded, usually with acute to acuminate tip, rarely with 3 broad, shallow lobes | broadly obtuse with cuspidate tip |
| Leaf margin: | entire | |
| Leaf adaxial surface: | yellow green, dull (147A); glabrous except for minute hairs along midvein | medium to dark green (147A); glabrous except for sparse unbranched hairs along veins |
| Leaf abaxial surface: | yellow green (147B); densely stellate pubescent except on midvein which has minute, reddish-brown, crinkled non-branching hairs | light green (147B); dense, stellate pubescence everywhere except along main veins which are densely tomentose tomentose with unbranched hairs |
| Leaf length (cm): | 22.6 (18.0-28.5) [20] | 20.1 (16.8-24.1) |
| Leaf width (cm): | 12.7 (10.2-17.5) [20] | 15.3 (13.1-18.2) |
| Leaf ratio (l/w): | 1.8 (1.3-2.5) [20] | 1.3 (1.2-1.5) |
| Leaf petiole length (cm): | 10.7 (6.6-15.4) [20] | 6.4 (5-8.7) |
| Leaf 1° vein organization: | pinnate; veins terminating as a small points extended beyond the blade (minutely apiculate), to 1.2 mm in length | pinnate; veins terminating as small extended points or mucros at leaf margins |
| Leaf 2° vein organization: | ± parallel | |
| Leaf puckering: | medium | weak |
| Leaf variegation | none | |
| Leaf spines on lower leaf | none | |
| Leaf surface | none | |
| Leaf petiole | none | |
| Young shoot hairs | present | |
| Young shoot::density of hairs | medium | |
| Young shoot::type of hairs | short | |
| Young shoot::anthocyanin color | absent | |

TABLE 4-continued

Botanical description of 'AU Gulf Coast Gold' and comparison to 'AU Golden Sunshine'

| | 'Gulf Coast Gold' | 'Golden Sunshine' |
|---|---|---|
| FLOWER | | |
| Inflorescence type | dichasium | |
| Inflorescence #: | mean 1.6 (range 1-3) [20] | mean 2.2 (range 1-3) [32] |
| 1° Pedicel length (cm): | mean 2.8 (range 1.8-3.9) [20] | 3.7(2.5-4.6) [16] |
| 2° Pedicel length (cm): | mean 1.5 (range 1.2-2.1) [20] | 1.8 (1.4-2.1) [14] |
| Pedicel pubescence: | minutely short, dense, unbranched | minutely, densely tomentose; unbranched 5.7 (5-8) [26] |
| Sepal #: | mean 6.1 (range 5.0-7.0) [20] | |
| Sepal color: | yellow green (147A) to greyed orange (166C) along margin | gray-green to slightly rust-colored at margins |
| Sepal pubescence: | dense, minutely tomentose with rusty brown crinkled hairs | minutely, densely tomentose, unbranched |
| Flower per infloresence | mean 3.4 (range 3-5) [20] | |
| Flower color: | creamy white (155D) | |
| Flower width (cm): | mean 4.2 (range 1.6-4.8) | 5.0 (4.8-5.8) [14] |
| Petal orientation: | overlapping | distinct to overlapping |
| Petal # | mean 6.2 (range 5.0-8.0) [20] | 6.4 (5-9) [17] |
| Petal length (cm): | mean 2.0 (range 1.8-2.4) [20] | 2.1 (1.7-2.5) [2] |
| Petal width (cm): | mean 1.7 (range 1.3-2.0) [20] | 1.6 (1.4-2.1) [20] |
| Petal ratio (l/w): | mean 1.2 (range 1.0-1.4) [20] | 1.3 (1.0-1.6)[20] |
| Ovary shape: | globose | |
| Ovary pubescence: | white, densely lanose, thicker toward apex | minutely, densely pilose; unbranched |
| Style #: | mean 24.4 (range 19-31)[20] | 20 (17-22) |
| Style orientation: | spreading to upright | upright to spreading |
| Stamen #: | mean 40.9 (range 36-49) [20] | 85.4 (80-96) |
| Anther length (mm): | mean 3.3 (range 2.5-3.6) [20] | 3.0-4.0 |
| Chilling requirement hrs: | 700 | |
| FRUIT | | |
| Fruit: average size (g) | 96.8 (47.7-149.6) | 90.4 (47.9-147.0 |
| Fruit: length (mm) | 71.5 (52.1-82.0) | 66.8 (51.9-80.3) |
| Fruit: width (max) (mm) | 48.3 (38.4-62.8) | 48.4 |
| Fruit: L/A ratio (max width) | 1.48 | 1.38 |
| Fruit: width (min) (mm) (34.2-50.1) | 45.1 (37.3-51.8) | 44.7 |
| Fruit: LID ratio (min width) | 1.59 | 1.49 |
| Fruit: core diameter (max) (mm) | 14.1 (3.1-20.5) | 14.3 (3.2-21.7) |
| Fruit: core diameter (max) (mm) | 5.1 (2.3-11.5) | 5.6 (2.7-12.7) |
| Fruit: locule number (30-40) | 36.1 (31-40) | 36.8 |
| Fruit: peduncle length (mm) | 27.1 (19.7-31.7) | 28.7 (21.6-34.2) |
| Fruit: peduncle width (mm) | 2.32 (1.8-2.7) | 1.7 (1.2-2.6) |
| Fruit: general shape | cylindrical | |

TABLE 4-continued

Botanical description of 'AU Gulf Coast Gold' and comparison to 'AU Golden Sunshine'

| | 'Gulf Coast Gold' | 'Golden Sunshine' |
|---|---|---|
| Fruit: cross-section at median | round to rarely slightly compressed | round |
| Fruit: general shape of stylar end | rounded to somewhat pointed | rounded |
| Fruit: shape of shoulder on stalk end | rounded, narrow | rounded, flat |
| Fruit: skin color at harvest | grey-brown dark side N199B, light side N199D | brown |
| Fruit: skin color change during ripening | grey-brown, dark side N199B, light side N199D | absent |
| Fruit: skin color at maturity for consumption | grey-brown (N199A) | brown |
| Fruit: hairs | present | |
| Fruit: density of hairs | medium | light |
| Fruit: type of hairs | lanulose (minutely wooly) | tomentose |
| Fruit: hair length (mm) | short (to 1.0 mm) | short (0.05-0.15) |
| Fruit: concentration of hairs | uniform to slightly concentrated distally | uniform |
| Fruit: adherence of hairs to skin (when rubbed) | strong | weak |
| Fruit: core diameter (at largest diameter) | 10 mm (short diameter = 4.5 mm) | large (10.0 mm by 3.4 mm) |
| Fruit core shape (in cross-section) | round to elliptical | elliptical |
| Fruit: core woody spike | present | |
| Fruit: prominence of core woody spike | medium | |
| Fruit: outer pericarp color at maturity for consumption | yellow green (153C) | yellow-green (152C-152D) |
| Fruit: inner pericarp color (locules) at maturity for consumption | yellow green (153C to 153D) | yellow-green (148A) |
| Fruit: core color at maturity | greyed yellow (160C) | |
| Fruit: seed color at maturity in flesh | N200A, dark brown | brown (165C) |
| Fruit: seed color when dry | greyed orange 165A | |
| Fruit sweetness | high | |
| Fruit acidity | medium | |
| Storage: | successfully stored for 4 months at 33° F. | |
| Color Chart RHS Colour Chart: The Royal Horticulture Society, London 2001 | | |
| Outer Pericarp | 153C | |
| Inner Pericarp | 153D | |
| Fruit Core at Harvest | 160C | |
| Seed Color (in flesh) | 200A | |
| Seed Color (dry seed) | 165A | |
| Fruit skin at maturity | N199A | |
| Leaf Color: | | |
| Mature leaf after petal fall | | |
| Upper side of leaf | 147A | |
| Lower side of leaf | 147B | |

TABLE 4-continued

Botanical description of 'AU Gulf Coast Gold' and comparison to 'AU Golden Sunshine'

| | 'Gulf Coast Gold' | 'Golden Sunshine' |
|---|---|---|
| Flower petals: | | |
| Main body of petal | 155D | |
| Plant stem: | | |
| Exposed side | N199A | |

Notes regarding Table 4:

1. Horticulture terminology is used in accordance with revised UPOV guidelines for kiwi.

2. Characters of comparison cultivar 'AU Golden Sunshine' are noted opposite that character when significantly different.

3. 'AU Golden Sunshine' plants were observed in the same experimental planting as the new cultivar.

4. All dimensions are in millimeters unless otherwise stated; weights are in grams.

5. The R.H.S. 2001 Color Chart used to determine actual color.

6. The numbers in brackets, e.g., after any reported number is the number of total measurements made. The number in parentheses e.g., ( ) is the range of the measurement.

LITERATURE CITED

Huang, H., S. Wang, Z. Zhang, and J. Gong. 2003. Exploration of *Actinidia* genetic resources and development of kiwifruit industry in China. Acta Hort 610:29-43.

Jaeger, S. R., R. Harker, C. M. Triggs, A. Gunson, R. L. Campbell, R. Jackman and C. Requejo-Jackman. 2011. Determining consumer purchase intentions: The importance of dry matter, size and price of kiwifruit. J. Food Sci. 76(3):177-184.

Jiang, Z., S. Wang, R. Huang, Z. Zhang, and H. Huang. 2005. 'Wuzhi No3' kiwifruit. HortScience 40(6):1923-1924.

Patterson, K., J. Burdon and N. Lallu. 2003. 'Hort 16A' kiwifruit: Progress and issues with commercialization. Acta Hort. 610:267-273.

Ramnoguilhem, M. And J. L. Tailleur. 2005. Kiwi, p. 185-207. In: J. M. Lespinasse and E. Leterme (eds.). Growing Fruit Trees. W.W. Norton & Company, New York, USA.

Sale, P. R. 1983. Kiwifruit culture. Govt. Printing Office, Wellington, New Zealand. pp. 95.

Wall, C., W. A. Dozier, Jr., R. C. Ebel, B. S. Wilkins, F. M. Woods, and W. G. Foshee III. 2008. Vegetative and floral chilling requirements of four new kiwi cultivars of *Actinidia chinensis* and *A. deliciosa*. HortScience 43(3):644-647.

Wang, M. Y., E. MacRae, M. Wohlers and K. Marsh. 2011. Changes in volatile production and sensory quality of kiwifruit during fruit maturation in *Actinidia deliciosa* 'Hayward' and *A. chinensis* 'Hort 16A'. Postharvest Biol. and Technol. 59:16-24.

We claim:

1. A new and distinct variety of *Actinidia chinensis* Planch plant named 'AU Gulf Coast Gold' substantially as described and illustrated herein.

* * * * *